US012023118B2

(12) United States Patent
Steger

(10) Patent No.: US 12,023,118 B2
(45) Date of Patent: Jul. 2, 2024

(54) SURGICAL INSTRUMENT STERILE ADAPTER WITH OPTICAL COUPLER

(71) Applicant: Intuitive Surgical Operations, Inc., Sunnyvale, CA (US)

(72) Inventor: John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 125 days.

(21) Appl. No.: 17/475,259

(22) Filed: Sep. 14, 2021

(65) Prior Publication Data

US 2022/0000570 A1 Jan. 6, 2022

Related U.S. Application Data

(62) Division of application No. 16/192,332, filed on Nov. 15, 2018, now Pat. No. 11,160,621.

(Continued)

(51) Int. Cl.
*A61B 34/35* (2016.01)
*A61B 17/00* (2006.01)
(Continued)

(52) U.S. Cl.
CPC .............. *A61B 34/35* (2016.02); *A61B 34/20* (2016.02); *A61B 34/37* (2016.02); *A61B 34/76* (2016.02);
(Continued)

(58) Field of Classification Search
CPC ......... A61B 34/35; A61B 34/20; A61B 34/37; A61B 34/76; A61B 90/361; A61B 17/3421; A61B 46/10; A61B 2017/00017; A61B 2017/00398; A61B 2017/00477; A61B 2034/2061; A61B 2034/305;
(Continued)

(56) References Cited

U.S. PATENT DOCUMENTS 5,212,752 A 5/1993 Stephenson et al.
6,331,181 B1 * 12/2001 Tierney .................. A61B 34/37
606/130

(Continued)

OTHER PUBLICATIONS

Ferrule Connectors Design, "Fiber Optic Couplers: Butt-jointed Optical Connector", 1 page, Retrieved from the internet [URL: http://constructionmanuals.tpub.com/14026/css/Fiber-Optic-Couplers-196.htm].

(Continued)

*Primary Examiner* — Gary Jackson
*Assistant Examiner* — Alexander M Eisenberg
(74) *Attorney, Agent, or Firm* — Schwegman, Lundberg & Woessner, P.A.

(57) ABSTRACT

A connector system is provided to connect a carriage that includes a rotatable drive member to a surgical instrument that includes a driven member, comprising. a mechanical interface that includes a drive transmission member configured to receive a rotational drive force provided by the drive member at the internal surface region and to provide a corresponding rotational drive force to the driven member at the external surface region; and a support to mount an end portion of an optical fiber to the mechanical interface with a center axis of the first end portion aligned with an axis of rotation of the drive transmission member.

11 Claims, 14 Drawing Sheets

Related U.S. Application Data

(60) Provisional application No. 62/588,083, filed on Nov. 17, 2017.

(51) Int. Cl.
*A61B 34/00* (2016.01)
*A61B 34/20* (2016.01)
*A61B 34/37* (2016.01)
*A61B 46/10* (2016.01)
*A61B 90/00* (2016.01)
*A61B 17/34* (2006.01)
*A61B 34/30* (2016.01)

(52) U.S. Cl.
CPC .. *A61B 90/361* (2016.02); *A61B 2017/00017* (2013.01); *A61B 2017/00398* (2013.01); *A61B 2017/00477* (2013.01); *A61B 17/3421* (2013.01); *A61B 2034/2061* (2016.02); *A61B 2034/305* (2016.02); *A61B 46/10* (2016.02); *A61B 2090/064* (2016.02); *A61B 2090/0811* (2016.02); *A61B 2090/3614* (2016.02)

(58) Field of Classification Search
CPC ...... A61B 2090/064; A61B 2090/0811; A61B 2090/3614
See application file for complete search history.

(56) References Cited

U.S. PATENT DOCUMENTS

| | | | |
|---|---|---|---|
| 6,736,547 B2* | 5/2004 | Stevens | G02B 6/3846 |
| | | | 385/61 |
| 6,770,081 B1 | 8/2004 | Cooper et al. | |
| 7,727,244 B2 | 6/2010 | Orban, III et al. | |
| 8,463,439 B2 | 6/2013 | Blumenkranz et al. | |
| 9,320,568 B2* | 4/2016 | Orban, III | A61B 46/10 |
| 2001/0028772 A1* | 10/2001 | Shirai | G02B 6/3821 |
| | | | 385/92 |
| 2006/0161138 A1 | 7/2006 | Orban, III et al. | |
| 2008/0249517 A1 | 10/2008 | Svanberg | |
| 2011/0277775 A1 | 11/2011 | Holop et al. | |
| 2013/0103050 A1 | 4/2013 | Richmond et al. | |
| 2013/0331650 A1* | 12/2013 | Blumenkranz | G01B 11/16 |
| | | | 600/130 |
| 2016/0018602 A1* | 1/2016 | Govari | G02B 6/3826 |
| | | | 385/71 |
| 2017/0100197 A1 | 4/2017 | Zubiate et al. | |
| 2017/0238822 A1 | 8/2017 | Young et al. | |
| 2019/0151037 A1 | 5/2019 | Steger | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SURGICAL INSTRUMENT STERILE ADAPTER WITH OPTICAL COUPLER

CLAIM OF PRIORITY

This application is a divisional of and claims the benefit of priority under 35 U.S.C. § 120 to U.S. patent application Ser. No. 16/192,332, filed on Nov. 15, 2018, which claims the benefit of priority under 35 U.S.C. § 119(e) to U.S. Provisional Patent Application Ser. No. 62/588,083, filed on Nov. 17, 2017, each of which is incorporated by reference herein in its entirety.

BACKGROUND

Minimally invasive medical techniques are intended to reduce the amount of tissue that is damaged during diagnostic or surgical procedures, thereby reducing patient recovery time, discomfort, and deleterious side effects. Teleoperated surgical systems that use robotic technology (so-called surgical robotic systems) may be used to overcome limitations of manual laparoscopic and open surgery. Advances in telepresence systems provide surgeons views inside a patient's body, an increased number of degrees of motion of surgical instruments, and the ability for surgical collaboration over long distances. In manual minimally invasive surgery, surgeons feel the interaction of the instrument with the patient via a long shaft, which eliminates tactile cues and masks force cues. In teleoperation surgery systems, natural force feedback is largely eliminated because the surgeon no longer manipulates the instrument directly. Kinesthetic or force feedback systems typically measure or estimate the forces applied to the patient by the surgical instrument.

Moreover, support arms of a surgical system typically are in close proximity with surgical instruments during a diagnostic or surgical procedure. The servo motors, sensors, encoders, and electrical connections that are used to robotically control the support arms typically cannot be sterilized using conventional methods, e.g., steam, heat and pressure, or chemicals, because the system parts would be damaged or destroyed in the sterilization process. A sterile drape has been previously used to cover the support arms to prevent contamination of a sterile field by a non-sterile support arms.

SUMMARY

In one aspect, a connector system is provided to connect an actuator to a surgical instrument. A drive transmission interface is configured to transmit an actuation force from the actuator to the surgical instrument. A first optical fiber is provided having a first end face terminating in a first connector. A first alignment feature for the first connector is configured to interface with a first mating feature on the surgical instrument. A second alignment feature for the first connector is configured to interface with a second mating feature on the surgical instrument.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DESCRIPTION OF EMBODIMENTS

Teleoperated Surgical System

Figure 1:
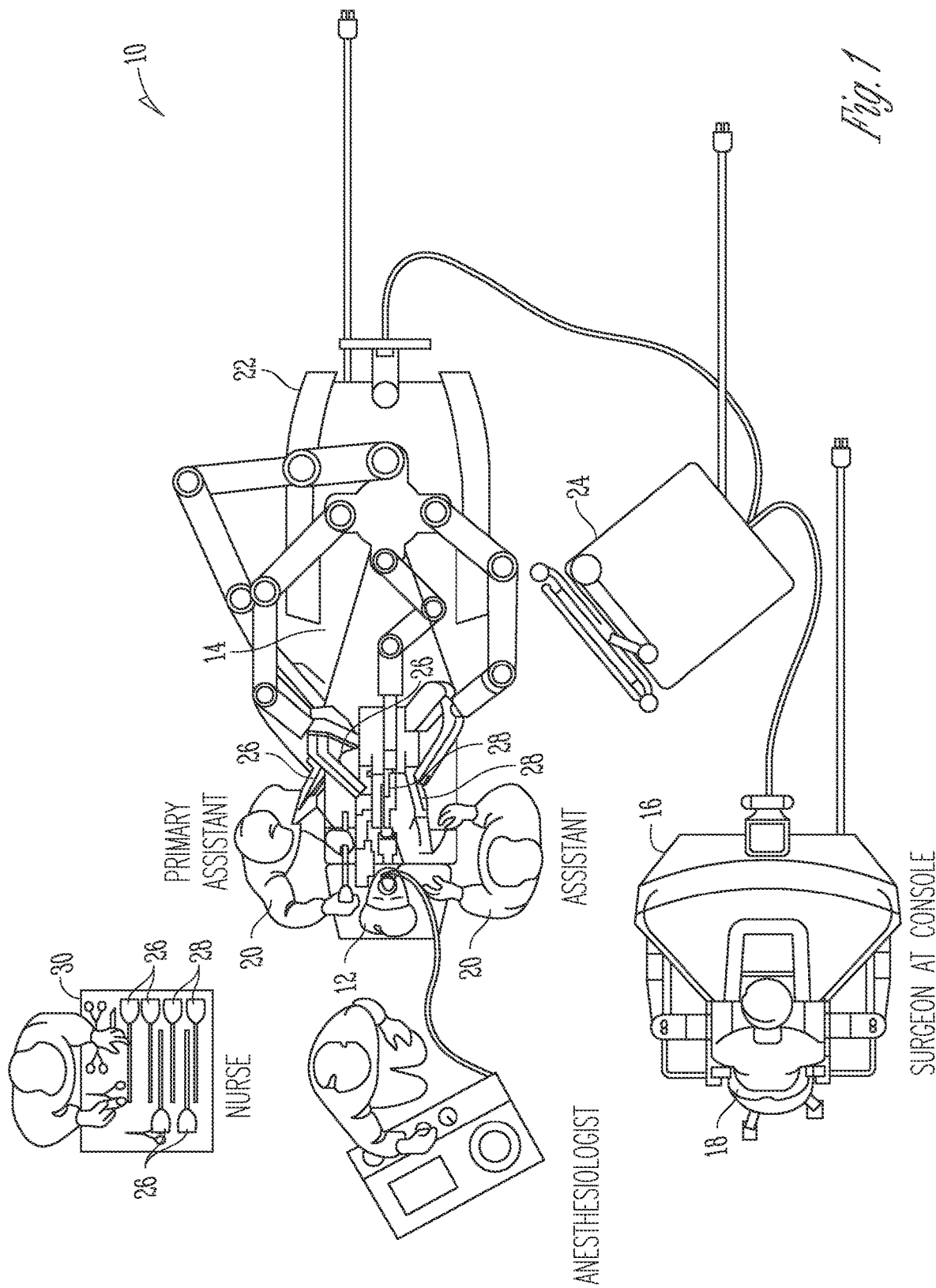
FIG. 1 is an illustrative plan view of a minimally invasive teleoperated surgical system.

FIG. 1 is an illustrative plan view of a minimally invasive teleoperated surgical system 10 for performing a minimally invasive diagnostic or surgical procedure on a patient 12 who is lying on an operating table 14. The system includes a surgeon's console 16 for use by a surgeon 18 during the procedure. One or more assistants 20 also may participate in the procedure. The minimally invasive teleoperated surgical system 10 further includes one or more patient-side carts 22 and an electronics cart 24. The patient-side cart 22 can manipulate at least one surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which may be manipulated by the patient-side cart 22 to orient the endoscope 28. Computer processors located on the electronics cart 24 may be used to process the images of the surgical site for subsequent display to the surgeon 18 through the surgeon's console 16. Moreover, the computer processors at the electronics cart 24 may be configured process optical signals indicative of forces imparted at the surgical instrument. The computer processor may produce haptic feedback at the surgeon's console 16, for example. In some embodiments, stereoscopic images may be captured, which allow the perception of depth during a surgical procedure. The number of surgical instruments 26 used at one time will generally depend on the diagnostic or surgical procedure and the space constraints within the operative site among other factors. If it is necessary to change one or more of the surgical instruments 26 being used during a procedure, an assistant 20 may remove the surgical instrument 26 from the patient-side cart 22, and replace it with another surgical instrument 26 from a tray 30 in the operating room.

Figure 2:
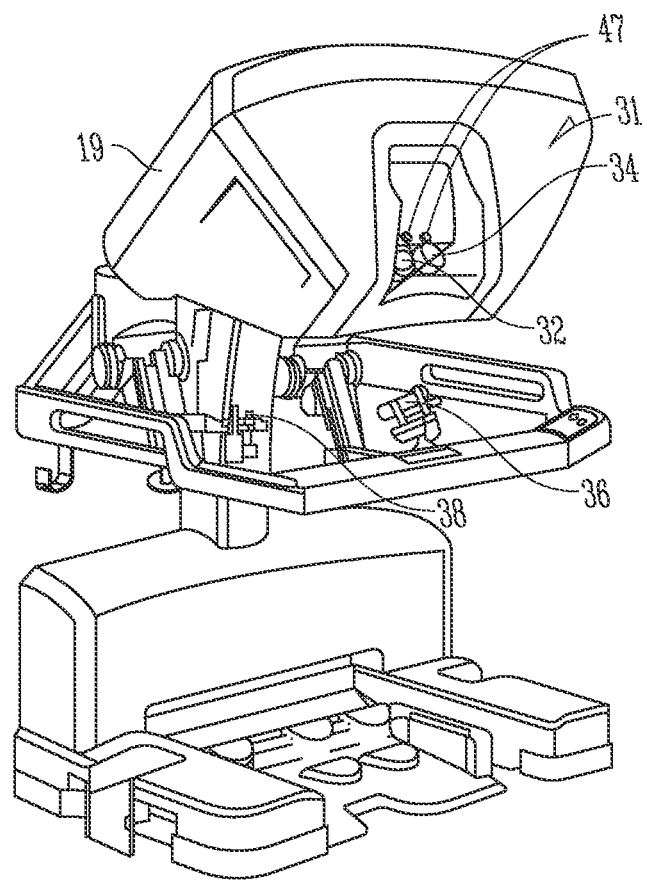
FIG. 2 is a perspective view of the surgeon's console of the minimally invasive teleoperated surgical system of FIG. 1.

FIG. 2 is a perspective view of the surgeon's console 16. The surgeon's console 16 includes a viewer display 31 that includes a left eye display 32 and a right eye display 34 for presenting the surgeon 18 with a coordinated stereoscopic view of the surgical site that enables depth perception. The console 16 further includes one or more hand-operated control inputs 36 to receive the larger-scale hand control movements. One or more surgical instruments installed for use on the patient-side cart 22 move in smaller-scale distances in response to surgeon 18's larger-scale manipulation of the one or more control inputs 36. The control inputs 36 may provide the same mechanical degrees of freedom as their associated surgical instruments 26 to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36, subject to communication delay constraints. Optical signals modulated based upon forces detected at force sensors (not shown) at the instrument 26 may be processed by the processors at the electronics cart 24 to produce haptic feedback at the control inputs 36 that is indicative of the detected forces.

Figure 3:
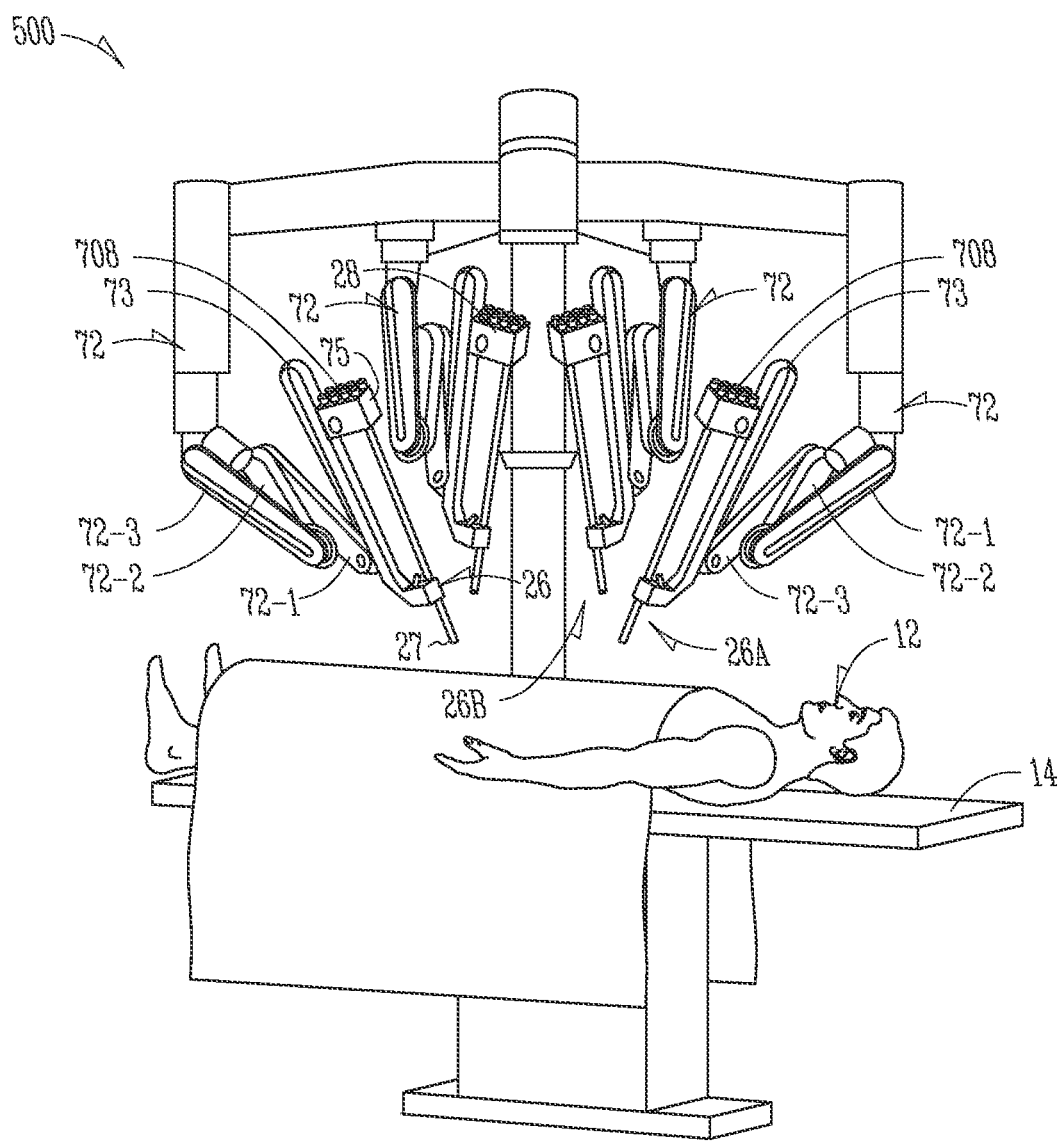
FIG. 3 is a perspective view of a patient-side cart of a minimally invasive teleoperated surgical system of FIG. 1.

FIG. 3 is a perspective view of a patient-side cart 22 of a minimally invasive teleoperated surgical system 10, in accordance with some embodiments. The patient-side cart 22 includes four mechanical support arms 72. Each support arm 72 includes first, second and third support arm segments 72-1, 72-2, 72-3 that are pivotally mounted end-to-end and a pivotally mounted support forearm 73. A respective surgical instrument carriage 75, which includes instrument motors to control instrument motion, is mounted at each support forearm 73. Additionally, each support arm 72 can optionally include one or more setup joints (e.g., unpowered and/or lockable) at the junctions of the support arm segments and at the junction with the support forearm 73 that may be used to position the attached surgical instrument carriage 75 in relation to the patient for surgery. The surgical instrument 26 is detachably connected to the instrument carriage 75. While the patient-side cart 22 is shown as including four surgical instrument carriages 75, more or fewer surgical instrument carriages 75 may be used. A teleoperated surgical system will generally include a vision system that typically includes an endoscopic camera instrument 28 for capturing video images and one or more video displays for displaying the captured video images.

In one aspect, for example, individual surgical instruments 26 and cannulas 27 are removably coupled to the carriages 75, with the surgical instrument 26 inserted through the cannula 27. One or more teleoperated actuator at the carriages 75 move the surgical instrument 26 as a whole. In one aspect, the instrument carriage 75 houses one or more teleoperated actuator (not shown) inside that provide a number of controller motions that the surgical instrument 26 translates into a variety of movements of an end effector on the surgical instrument 26. Thus, the teleoperated actuators in the instrument carriage 75 move individual components of the surgical instrument 26 such as end effector wrist movement or jaw movement, for example.

A surgeon manipulates the control inputs 36 to control an instrument's individual components. An input provided by a surgeon or other medical person to the control input 36 (a "master" command) is translated into a corresponding action by the surgical instrument 26 (a "slave" response) through actuation of one or more remote motors. A wire cable-based force transmission mechanism or the like is used to transfer the motions of each of the remotely located teleoperated motors to a corresponding instrument-interfacing actuator output located at an instrument carriage 75. In some embodiments, a mechanical adapter interface 76 mechanically couples an instrument 26 to actuators within an instrument carriage. A first actuator (not shown), which controls a first motion of the surgical instrument such as longitudinal (z-axis) rotation. The surgical instrument 26 is mechanically coupled to a second actuator, which controls second motion of the surgical instrument such as two-dimensional (x, y) motion. The surgical instrument 26 is mechanically coupled to a third actuator, which controls third motion of the surgical instrument such as opening and closing of jaws of an end effector, for example.

Figure 4:
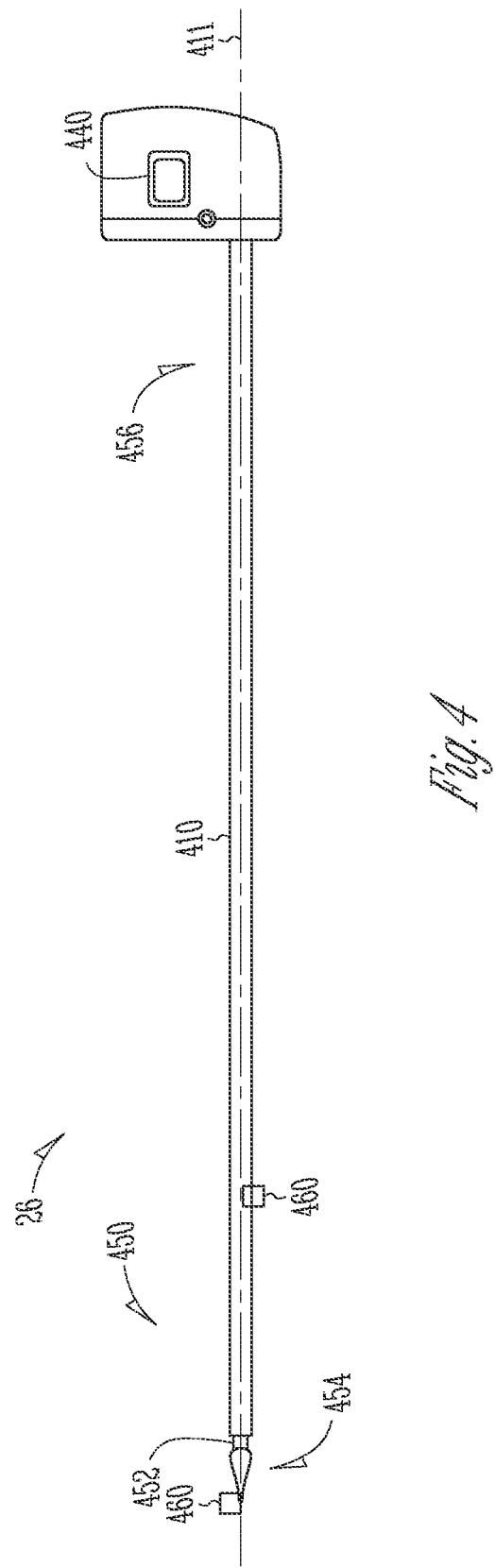
FIG. 4 is an elevation view of a surgical instrument.

FIG. 4 is a perspective view of a surgical instrument 26, which includes an elongated hollow cylindrical tubular shaft 410 having a distal (first) end portion 450 for insertion into a patient's body cavity and proximal (second) end portion 456 that is secured to a proximal instrument controller 440. The shaft 410 includes a longitudinal center axis 411 (shaft axis). The proximal instrument controller 440 is configured to exert force upon wire cables (not shown) that extend within the shaft 410, in response to mechanical control inputs provided by actuators (not shown) within an instrument carriage 75. The wires are operatively coupled so that movement of the wires may impart motion to an end effector 454 such as to open or close of jaws and (x, y) wrist motion, for example. Different instruments may have different end effectors 454 that have different configurations of wires that require different proximal instrument controllers. As discussed more fully below with reference to FIG. 7, a mechanical adapter interface 76 can adapt drive elements (not shown) of the carriage 75 to a driven elements (not shown) of particular mechanical adapter interface 76. One or more force sensors 460 may be disposed at the end effector 454 or within the shaft 410, for example. The surgical instrument 26 is used to carry out surgical or diagnostic procedures. The distal portion 450 of the surgical instrument 26 can provide any of a variety of end effectors 454, such as the forceps, a needle driver, a cautery device, a cutting tool, an imaging device (e.g., an endoscope or ultrasound probe), or the like. A surgical end effector 454 can include a functional mechanical degree of freedom, such as jaws that open or close, or a knife that translates along a path or a wrist 452 that may move in x and y directions. Thus, actuators located at the carriage 75 near the proximal end portion 456 of the shaft 410 control movement of the end effector 454 at the distal end portion 450 of the shaft 410 by causing the proximal instrument controller 440 to exert forces upon wires (not shown) extending within the shaft 410 between the motors and the end effector.

Sterile Adapter

Figure 5A:
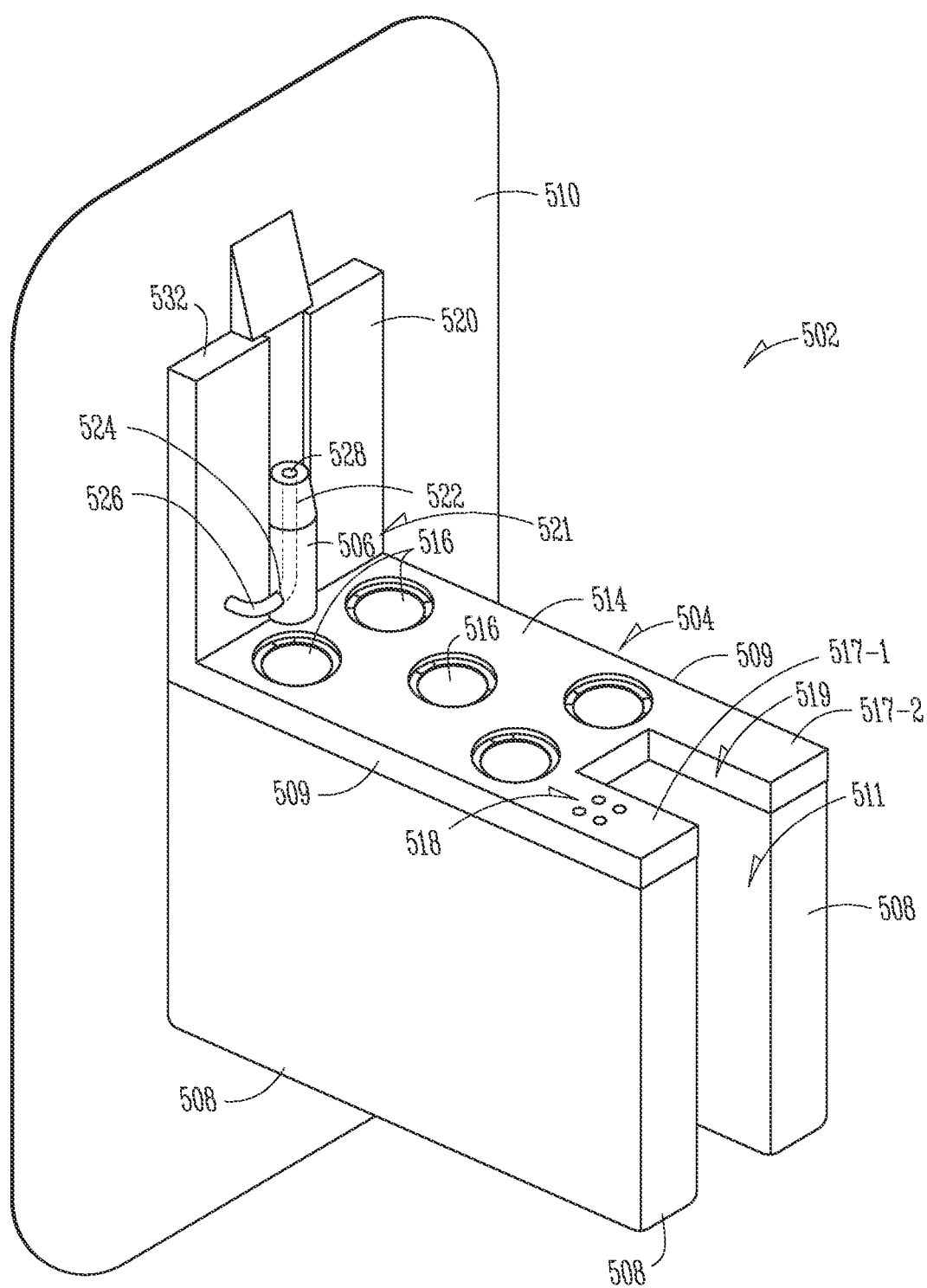
FIGS. 5A-5C are an illustrative top perspective view (FIG. 5A) and bottom perspective view (FIG. 5B) and rear perspective view (FIG. 5C) of a sterile adapter, in accordance with some embodiments.
Figure 5B:
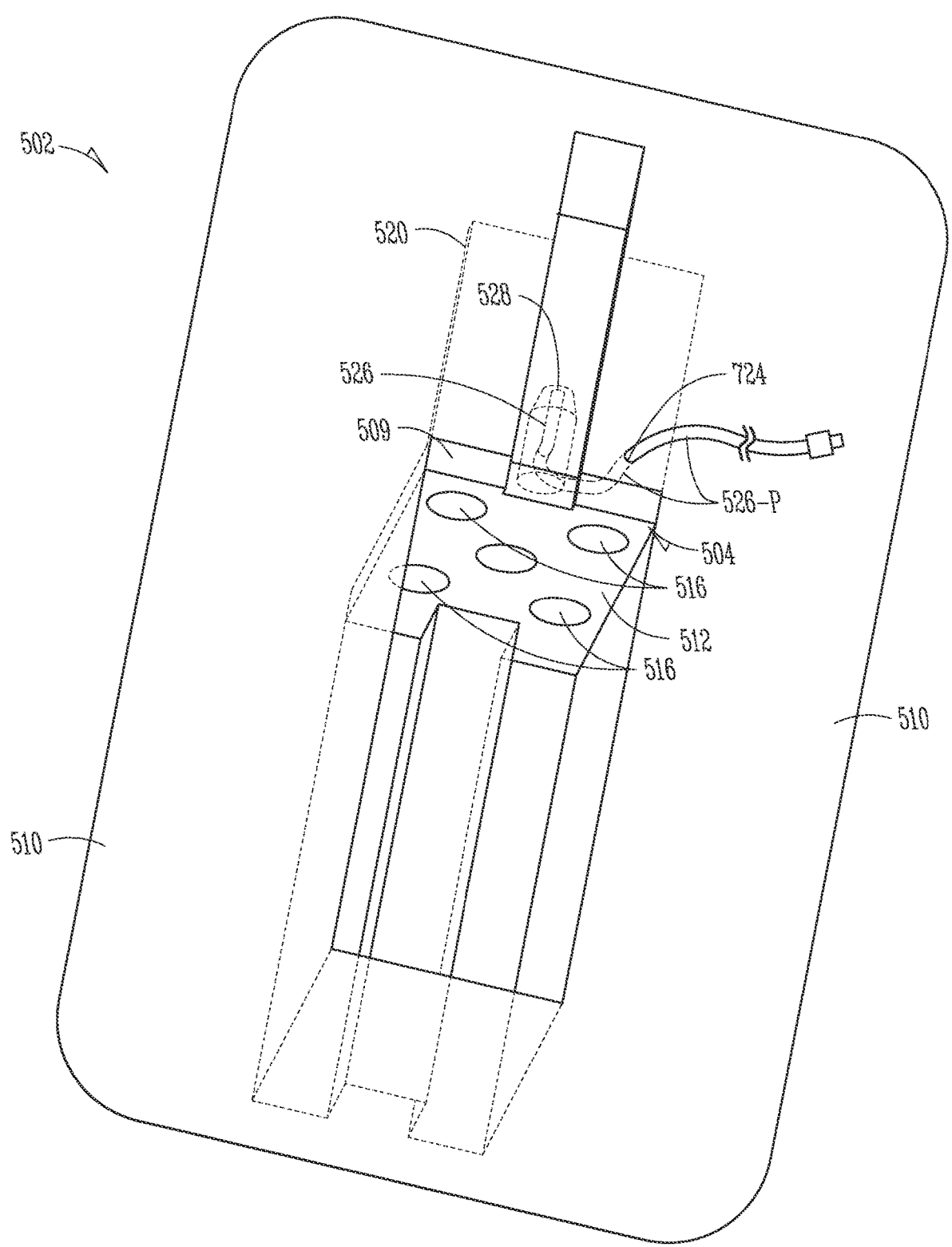
Figure 5C:
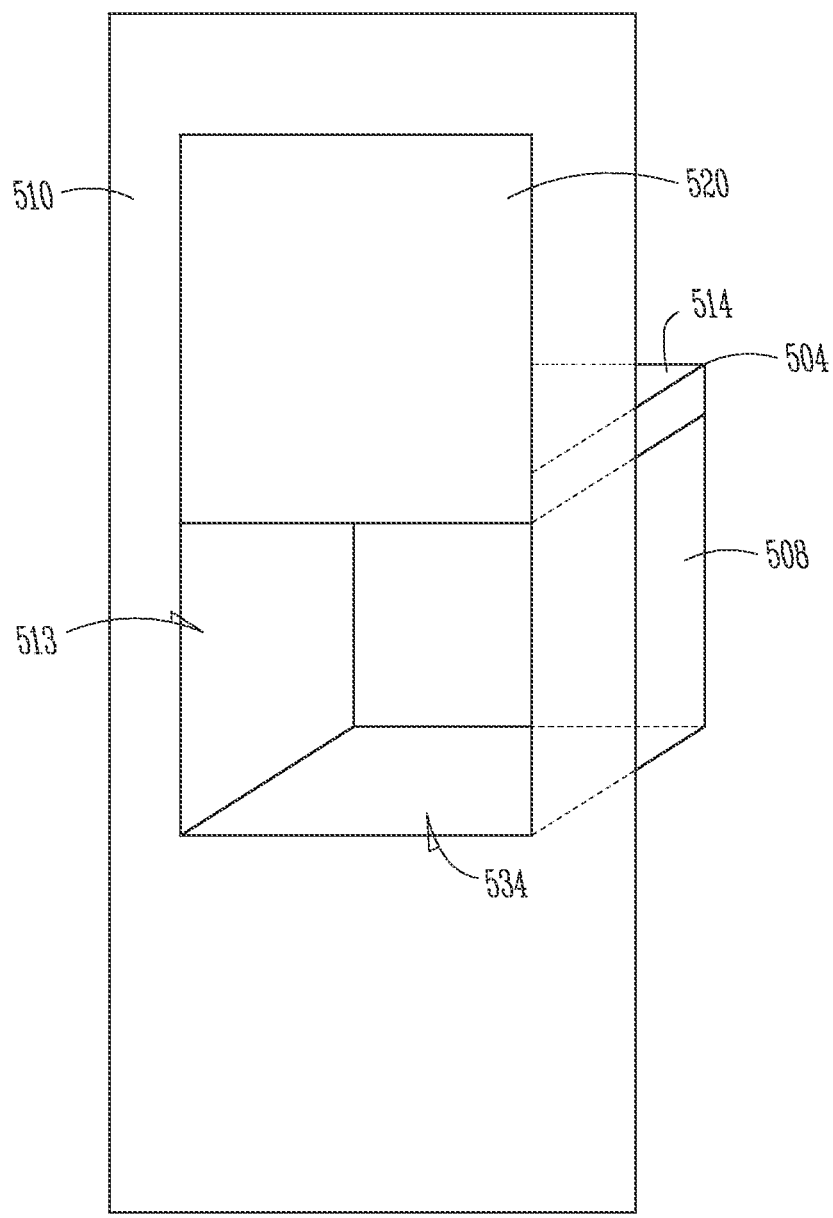

FIGS. 5A-5C are an illustrative top perspective view (FIG. 5A) and bottom perspective view (FIG. 5B) and rear perspective view (FIG. 5C) of a sterile adapter 502 in accordance with some embodiments. The sterile adapter 502 includes a mechanical adapter interface 504, a first housing 506 that supports a first end portion of a first optical fiber 526, an integral protective pouch 508, and a planar flange drape 510. The mechanical adapter interface 504 and the support 506 are solid material structures. The pouch 508 and the flange drape 510 are flexible, foldable structures formed of durable materials such as polyethylene, polyurethane, polycarbonate, or mixtures thereof, for example.

The mechanical adapter interface 504 includes a support structure frame 509 that acts as a transmission interface that includes an internal non-sterile surface region 512 that faces inward toward the pouch 508 and an external sterile surface region 514 that faces outward away from the pouch 508. Figure 5B shows the internal surface region 512 of the pouch 508. The support frame structure 509 mounts a plurality of force transmission members. In some embodiments, the force transmission members include a plurality of rotatable drive transmission interface members 516 mounted upon the support structure frame 509 to transmit drive forces from one or more rotatable drive members driven by actuators of an instrument carrier 75 that can be disposed within a pouch cavity 513 defined by the pouch, to one or more rotatable driven members of a proximal instrument controller 440 that can be mounted upon the external surface region 514 outside the pouch 508. Note that while rotatable force transmission members are depicted and described for exemplary purposes, in various other embodiments, any other type of actuation mechanism modality can be incorporated, such as linear drive, rocker/pulley drive, and gear drive, among others.

The support frame 509 also defines electrical connector openings 518 for passage of electrical connectors (not shown). A distal side of the support frame 509 includes first and second prongs 517-1, 517-2 that define a notch region 519 between them for passage of an instrument shaft 410. The mechanical adapter interface 504 acts, not only to couple mechanical forces from a carriage to a proximal instrument controller 440, but also as a protective barrier to block contaminants within the pouch from entering a sterile surgical field external to the pouch. U.S. Pat. No. 6,331,181, entitled "Surgical Robotic Tools, Data Architecture, and Use" at its FIGS. 7A-7I and corresponding portions of the specification discloses details of an alternative example mechanical adapter interface.

The first housing 506 (first housing) is integrally formed with an upstanding guide wall 520 that upstands from the external surface region 514 at a proximal peripheral portion of the support frame 509. More particularly, the first housing 506 upstands from a base portion 521 of the upstanding guide wall 520 and defines an internal first housing cavity indicated by dashed lines 522 to receive a first optical connector portion (not shown). The first housing 506 defines a first hole 524 near the base portion 521 of the upstanding guide wall 520 adjacent the external surface region 514 of the support frame 509 sized for passage of a first optical fiber 526. The first housing 506 aligns a first optical connector portion (not shown) disposed within the first housing cavity 522 parallel with the axes of rotation of the rotatable drive transmission interface members 516. The first housing 506 defines a second hole 528 sized for passage of an end portion of second optical fiber, explained below. The first housing 506 extends partway along a distal surface (facing the external surface region 514) of the upstanding guide wall 520 in alignment with a first alignment groove 530 defined by the upstanding guide wall 520 that extends between the second hole 528 formed in the first housing 506. and an outer peripheral rim 532 of the upstanding guide wall 520. The first alignment groove 530 acts as a first alignment feature to provide coarse alignment with an optical connector portion housing 702 (second housing) that acts as a first mating feature of a proximal instrument controller 440 of a surgical instrument 26.

The pouch 508 is bonded to an outer perimeter of the support frame 509 and defines the pouch cavity 513 sized to fit a carriage 75. More particularly, the pouch 506 defines a proximal opening 534 sized for passage of a carriage 75. During installation, a user can slide the pouch over the carriage through the pouch opening 534. The pouch cavity 513 has an inner contour shaped to generally match the shape of the carriage 75 and to fit loosely about the carriage, which is mounted on a support forearm 73. The pouch 508 follows the contours of the notch region 519 and defines an elongated notch-channel 536 that provides a three-sided protective barrier between an instrument shaft 410 and a carriage 75 within the pouch cavity 513. The pouch 508 encloses a carriage 75 to act as a protective barrier to block contaminants on the carriage 75 within the pouch 508 from entering a sterile surgical field external to the pouch 508.

The peripheral flange drape 510 extends outward from a proximal portion of the pouch behind the upstanding guide wall 520. The flange drape 510 extends outward from the proximal opening 534 in the pouch 508 and may be positioned against an external surface of another protective drape, explained below, that extends over a support forearm 73 to provided added isolation of a non-sterile carriage 75 inside the pouch 508 from a sterile surgical field outside the pouch 508. Moreover, the upstanding guide wall 520 may be secured against a support forearm 73 with a strap (not shown), for example, to more firmly secure the peripheral flange drape 510, which extends outwardly behind upstanding guide wall 520, against the support forearm 73 to further isolate a carriage 75 within the pouch 508 from a sterile external sterile field.

Overview of Mounting a Sterile Adapter and a Surgical Instrument

Figure 6A:
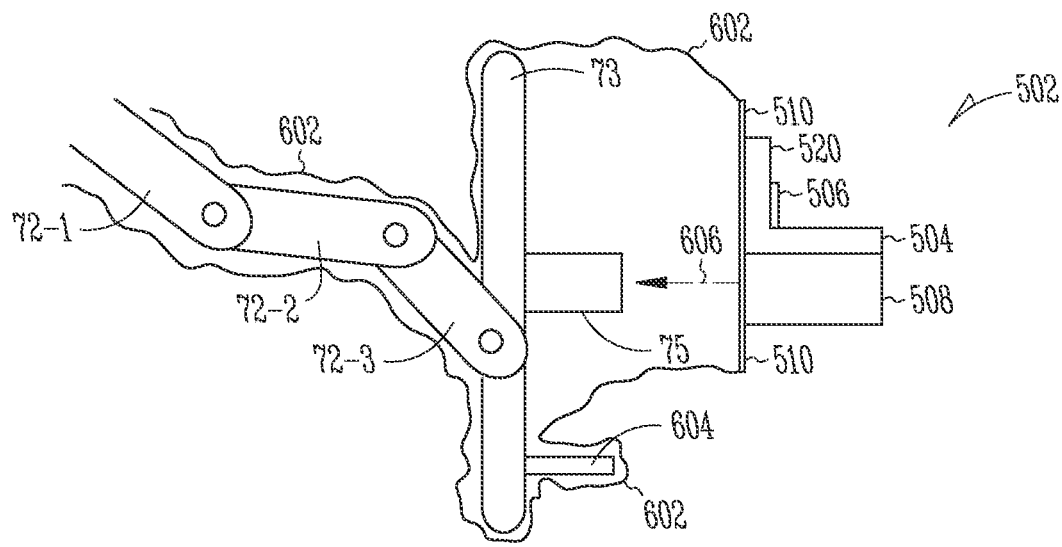
FIGS. 6A-6C are illustrative simplified drawings showing example of stages of installation of a drape, sterile adapter and surgical instrument, in accordance with some embodiments.
Figure 6B:
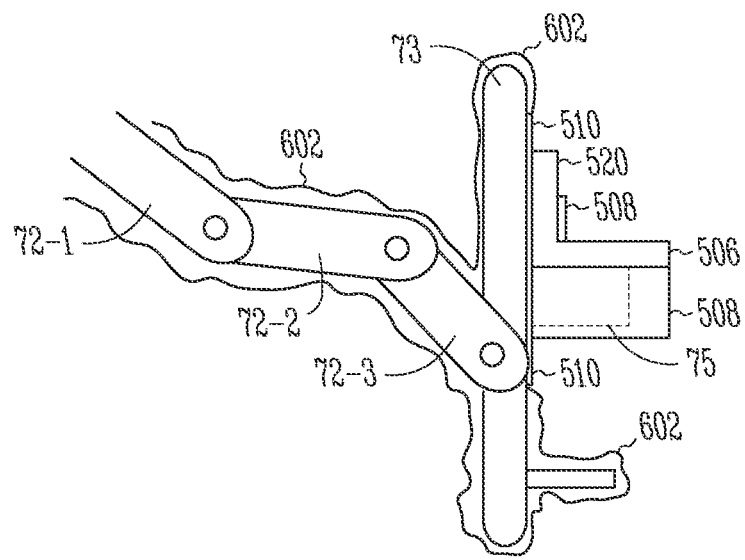
Figure 6C:
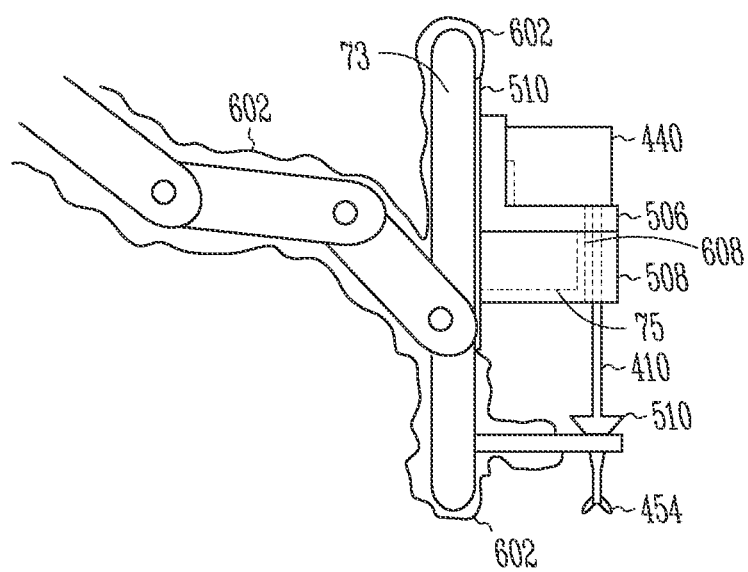

FIGS. 6A-6C are illustrative simplified drawings showing example of stages of installation of a drape, sterile adapter and surgical instrument. In each of these three drawings, a protective drape 602 is shown installed over a surgical system support arm 72. The drape 602 may be comprised of the same durable materials as the pouch 508. The support arm drape 602 may include multiple component drapes. U.S. Pat. No. 9,320,568, entitled "Sterile Surgical Drape" discloses sterile drapes in accordance with some embodiments.

FIG. 6A is an illustrative simplified side view showing installation of a protective drape 602 integrally formed with the sterile adapter pouch 508 over a support arm 72 with a sterile adapter 502 installed upon a carriage 75 mounted to the support arm 72. A cannula support 604 also is mounted upon the support arm 72, and the drape 602 covers cannula support 604. The drape 602 includes a sterile external surface that faces a sterile surgical field outside the drape. The drape 602 includes a non-sterile interior surface that faces the non-sterile support arm 72 covered beneath by the drape 602. Thus, it will be appreciated that as indicated by arrow 606, the drape 602 and the sterile adapter pouch 508 form a continuous protective barrier that may be installed over the carriage 75, a support forearm 73 on which the carriage 75 is mounted, and the support arm 72 on which the support forearm 73 is mounted.

FIG. 6B is an illustrative simplified side view showing the drape 602 installed over the support arm 72 and showing the sterile adapter 502 installed over the carriage 75. As explained above, the pouch 508 defines a pouch cavity 513 to receive the non-sterile carriage 75. The proximal flange drape 510 overlays an outer sterile portion of the drape 602 that in turn overlays a support forearm 73 on which the carriage 75 is mounted. Thus, the flange drape 510 provides a protective barrier between the pouch opening 534 through which the carriage 75 extends and the sterile field. Thus, the drape 602 in conjunction with the sterile adapter 502 with its pouch 508 maintain a sterile barrier between the support arm 72 and a sterile surgical field where a surgical procedure may be performed.

FIG. 6C is an illustrative simplified side view drawing showing the drape 602 installed over the support arm 72, showing the sterile adapter 502 installed over the carriage 75, and showing the surgical instrument 26 mounted upon the sterile adapter. The dashed lines 608 represent passage of a portion of the instrument shaft 410 within a groove defined by the carriage 75 and by the sterile adapter 502. It can be seen that a distal portion of the surgical instrument shaft extends within a sterile cannula 610 mounted to the cannula support 604 which is encompassed within the drape 602.

Optical and Mechanical Alignment

Figure 7:
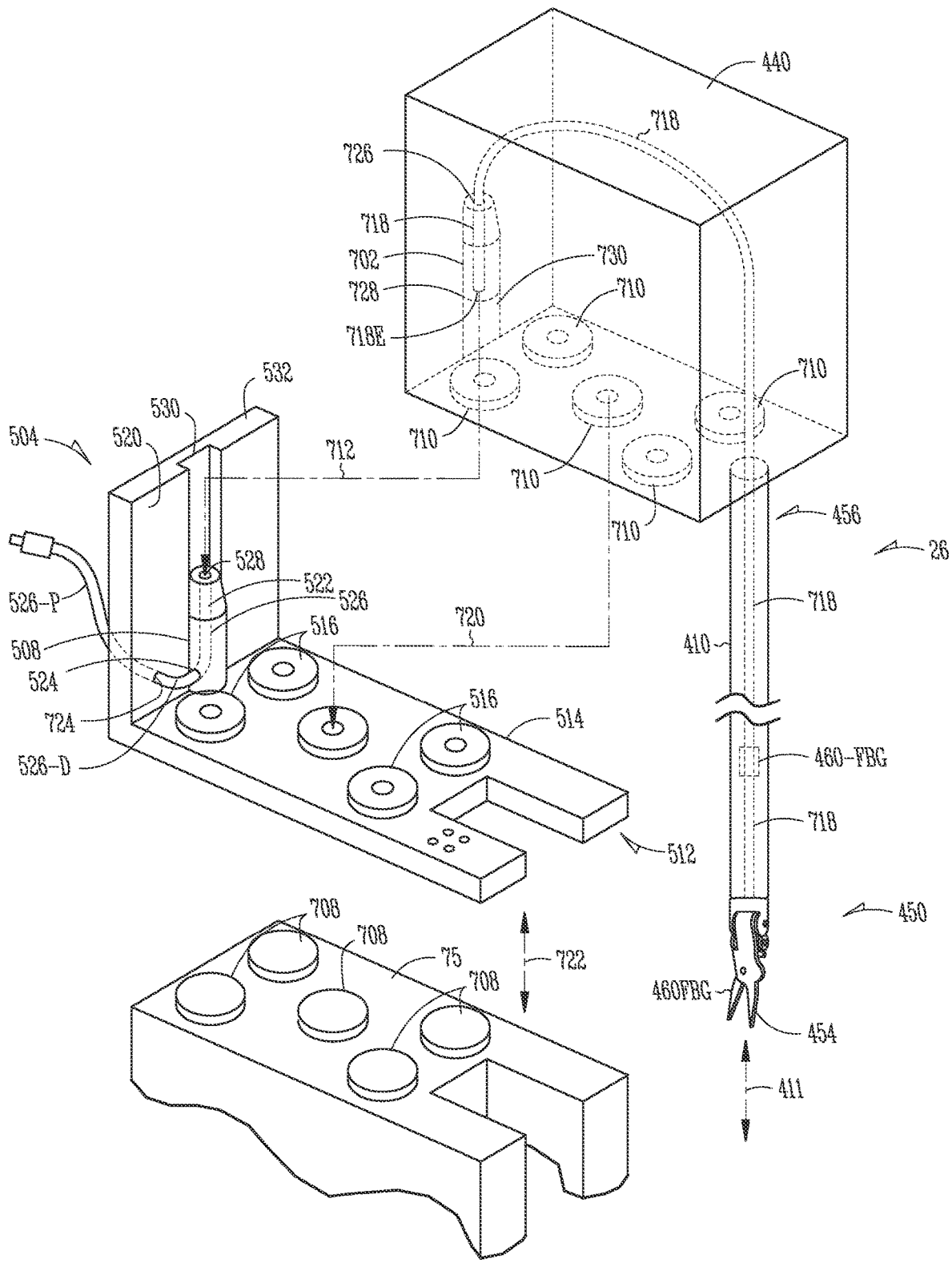
FIG. 7 is an illustrative simplified partially transparent perspective view of the mechanical adapter interface, a surgical instrument, and the carriage, in accordance with some embodiments.

FIG. 7 is an illustrative simplified partially transparent perspective view of the mechanical adapter interface 504, a surgical instrument 26, and a portion of a carriage 75 in accordance with some embodiments. FIG. 7 shows alignment of an optical connector portion housing 506 (first housing) on the mechanical adapter interface 504 with an optical connector portion housing 702 (second housing) on a proximal instrument controller 440 of the surgical instrument 26. FIG. 7 also indicates alignment of rotatable drive members 708 of the carriage 75 with the rotatable drive transmission interface members 516 of the mechanical adapter interface 504 and alignment of the rotatable drive transmission interface members 516 with rotatable driven members 710 of the proximal instrument controller 440. Arrow 712 indicates that during installation of the surgical instrument upon the mechanical adapter interface 504, an end face portion 526E of the first optical fiber 526 that extends within the first housing 506 is aligned with an end face portion 718E of a second optical fiber 718 that extends within the second housing 702. Arrow 720 indicates that during installation, the rotatable drive transmission members 516 mounted on the mechanical adapter interface 504 are aligned with the rotatable driven members 710 mounted to an engagement face of the proximal instrument controller 440. Arrow 722 indicates that during installation, the rotatable drive transmission members 516 mounted on the mechanical adapter interface 504 are aligned with the rotatable drive members 708 mounted to an engagement face of the carriage 75.

The first optical fiber 526 extends through a first hole 524 formed in the upstanding guide wall 520. A proximal portion of the first optical fiber 526-$p$ is disposed on a proximal side of the upstanding guide wall 520 and a distal portion of the first optical fiber 526-$d$ is disposed on a distal side of the upstanding guide wall 520. The distal side portion of the first optical fiber 526-$d$ enters the first housing 506 through the first hole 524 near the base portion of the upstanding guide wall 520 and extends within the first housing 506, as indicated by dashed lines 526, perpendicular to the mechanical adapter interface support frame internal and external surfaces 512, 514.

The second optical fiber 718 extends between a distal end portion 450 and a proximal end portion 456 of a surgical instrument shaft 410 and extends between the proximal end portion 456 of the surgical instrument shaft and the second housing 702. The shaft 410 and the proximal instrument controller 440 are shown partially transparent with other internal components invisible in order to simplify the explanation of the path of the second optical fiber 718. The second optical fiber 718 may be used to transmit optical signals indicative of force imparted to an end effector 454 and/or to the instrument shaft 410. Force may be sensed using fiber Bragg grating sensors 460-FBG, for example. The second optical fiber 718 extends into the second housing 702 through a fourth hole 726 formed in the second housing 702 and extends within the second housing 702 perpendicular to the to a shaft axis 411 the shaft. The end face portion 718E of the second fiber 718 extends out from a fifth hole 728 formed in the second housing 702. A proximal surface of the proximal control mechanism 440 defines a second alignment groove 730 aligned with the fifth hole 728 and the end face portion 718E of the second fiber 718 that protrudes from it.

Figure 8:
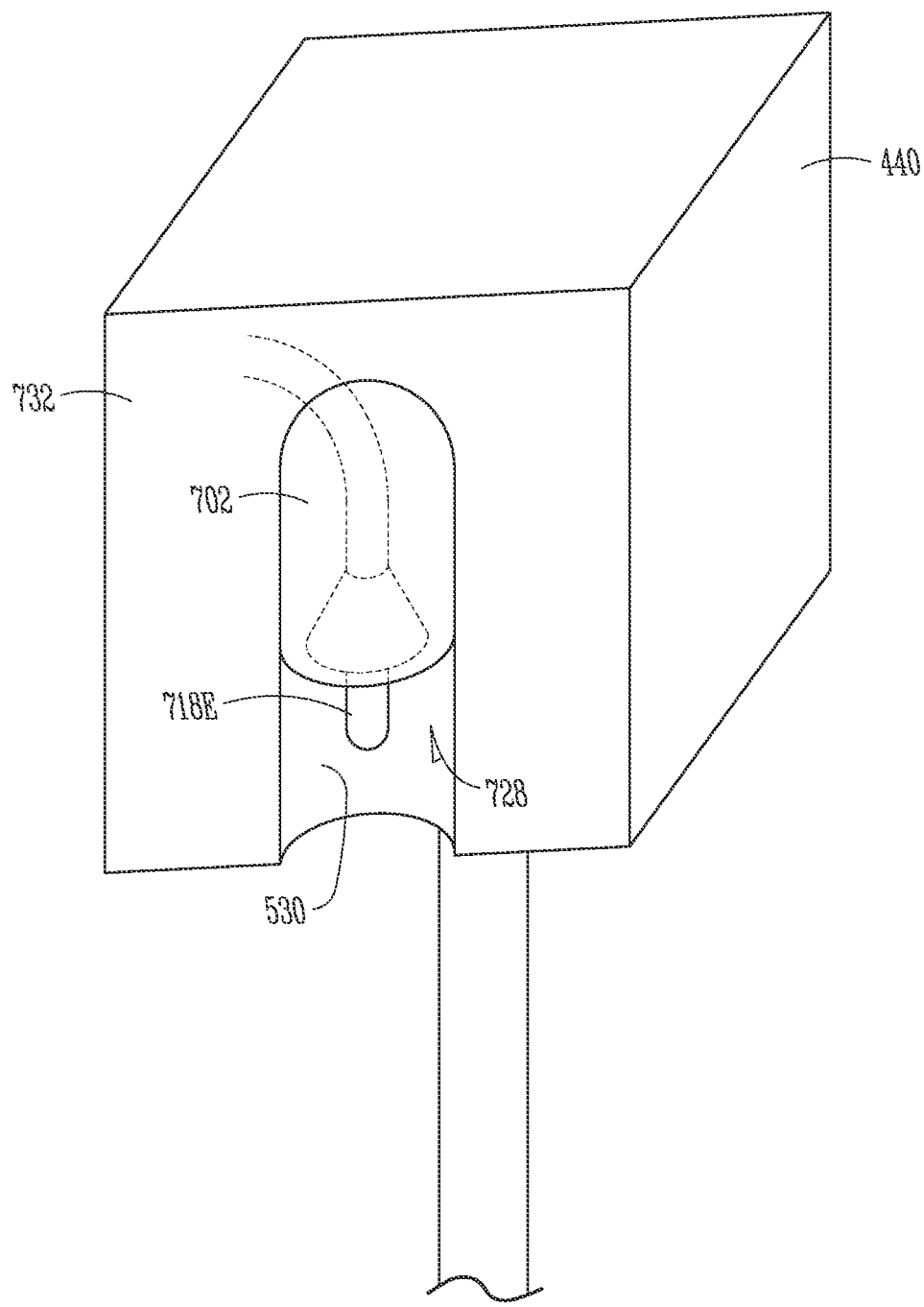
FIG. 8 is an illustrative perspective proximal view of a surgical instrument proximal instrument controller and a portion of a shaft, in accordance with some embodiments.

FIG. 8 is an illustrative perspective proximal view of a surgical instrument proximal instrument controller 440 and a portion of a shaft 410, in accordance with some embodiments. An end face portion 718E of the second optical fiber 718 is shown protruding from the fifth hole 728 formed in the second housing 702. The end face portion 718E of the second optical fiber 718 extends outward from the fifth hole 728 in alignment with the second alignment groove 730 formed in the proximal surface region 732 of the proximal instrument controller 440. It will be appreciated from FIGS. 7-8 that the second alignment groove 730 aids in alignment of an outer surface of the first housing 506 and the first alignment groove 530 aids in alignment of an outer surface of the second housing 702 such that the end face portion 718E of the second optical cable 718 that protrudes from the second housing 702 aligns with the end face portion 526E of the first optical fiber 526 that extends within the first housing 506.

Figure 9:
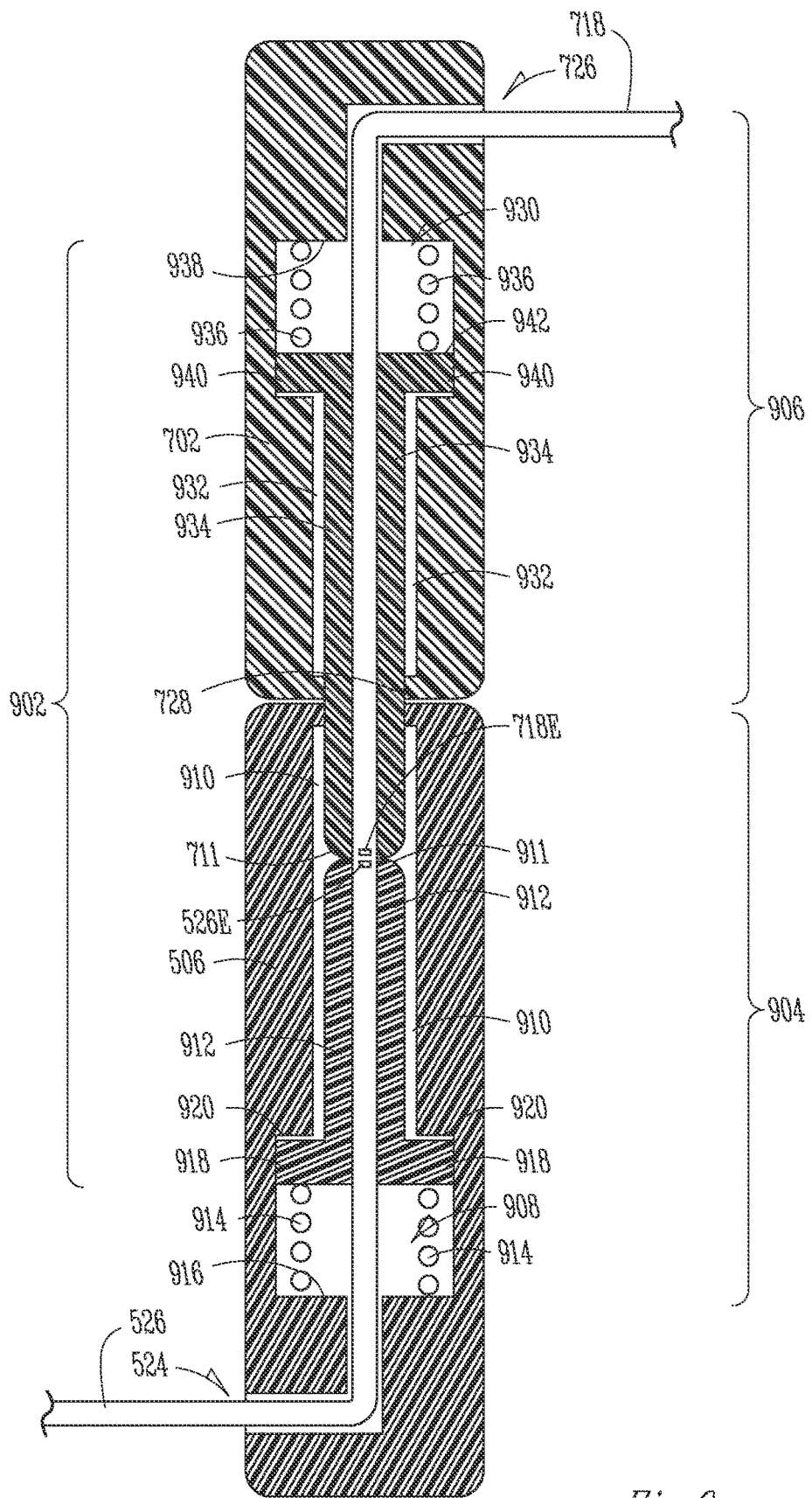
FIG. 9 is an illustrative drawing showing an optical connector comprising an optical fiber connector portion in a first housing on a sterile adapter and an optical fiber connector portion in a second housing on surgical instrument, in accordance with some embodiments.

FIG. 9 is an illustrative drawing showing an optical connector 902 in which the first and second optical connector portions 904, 906 cooperate to align end faces portions 526E, 718E of the first and second optical fibers 526, 718 so that they may transmit optical signals between them. The first housing 506 defines a first housing cavity 908 in which a first guide sleeve 910, a first ferrule 912, and a first spring 914 are mounted. The first optical fiber 526 extends through the third hole 524 formed in the first housing 506 to access the first housing cavity 908. The first ferrule 912 engages an end portion of the first optical fiber 526 disposed within the first housing cavity 908 such that an end face portion 526E of the first optical fiber 526 is aligned with an end tip portion 911 of the first ferrule 912 and with the first hole 528 formed in the first housing 506. The first ferrule 912 is slideably mounted within the first guide sleeve 910. The first spring 914 is mounted upon a first shoulder 916 within the second housing 702 and configured to urge the first ferrule 912 into the first guide sleeve 910, The first ferrule 912 includes a stop surface 918 that engages a second shoulder 920 within the second housing 702 to limit its range of motion within the first guide sleeve 910.

The second housing 702 defines a second housing cavity 930 in which a second guide sleeve 932, a second ferrule 934, and a second spring 936 are mounted. The second optical fiber 918 accesses through the fourth hole 726 formed in the second housing 702. The second ferrule 934 engages end face portion 718E of a second optical fiber 718 disposed within the second housing cavity 930 such that an end face portion 718E of the second optical fiber 718 is aligned with an end tip portion 711 of the second ferrule 934. The end face portion 718E of the second optical fiber 718 and the tip portion 711 of the second ferrule 934 protrude out through the fifth hole 728 formed in the second housing 702. The second ferrule 934 is slideably mounted within the second guide sleeve 932. The second spring 936 is mounted upon a third shoulder 938 within the second housing 702 and configured to urge the second ferrule 934 into the second guide sleeve 932. The second ferrule 934 includes a stop surface 940 that engages a fourth shoulder 942 within the second housing 702 to limit its range of motion within the second guide sleeve 932. The first guide sleeve 910 acts as a second alignment feature to provide fine alignment with the second ferrule 934 that acts as a second mating feature of a proximal instrument controller 440 of a surgical instrument 26.

In accordance with some embodiments, the second ferrule 934 is configured to extend outward through the fifth hole 728. When the first and second housings 506, 702 are aligned using the first and second alignment grooves 530, 730, the second ferrule 934 and the second optical fiber end face portion 718E project into the second hole 528 formed in the first housing 506. The first and second springs 914, 936 urge the first and second optical fiber end faces 526E, 718E into abutting contact. The end faces 526E, 718E of the first and second optical fibers 526, 718 are polished such that optical signals can be transmitted between the first and second optical fibers 526, 718 while their end faces 526E, 718E abut. The first guide sleeve 910 acts as a second alignment feature to provide fine alignment with the second ferrule 934 that acts as a second mating feature of a proximal instrument controller 440 of a surgical instrument 26. The end tip portion 911 of the first ferrule 912 acts as third alignment feature to provide alignment with the end tip portion 711 of the second ferrule 934 that acts as a third mating feature of a proximal instrument controller 440 of a surgical instrument 26.

Figure 10:
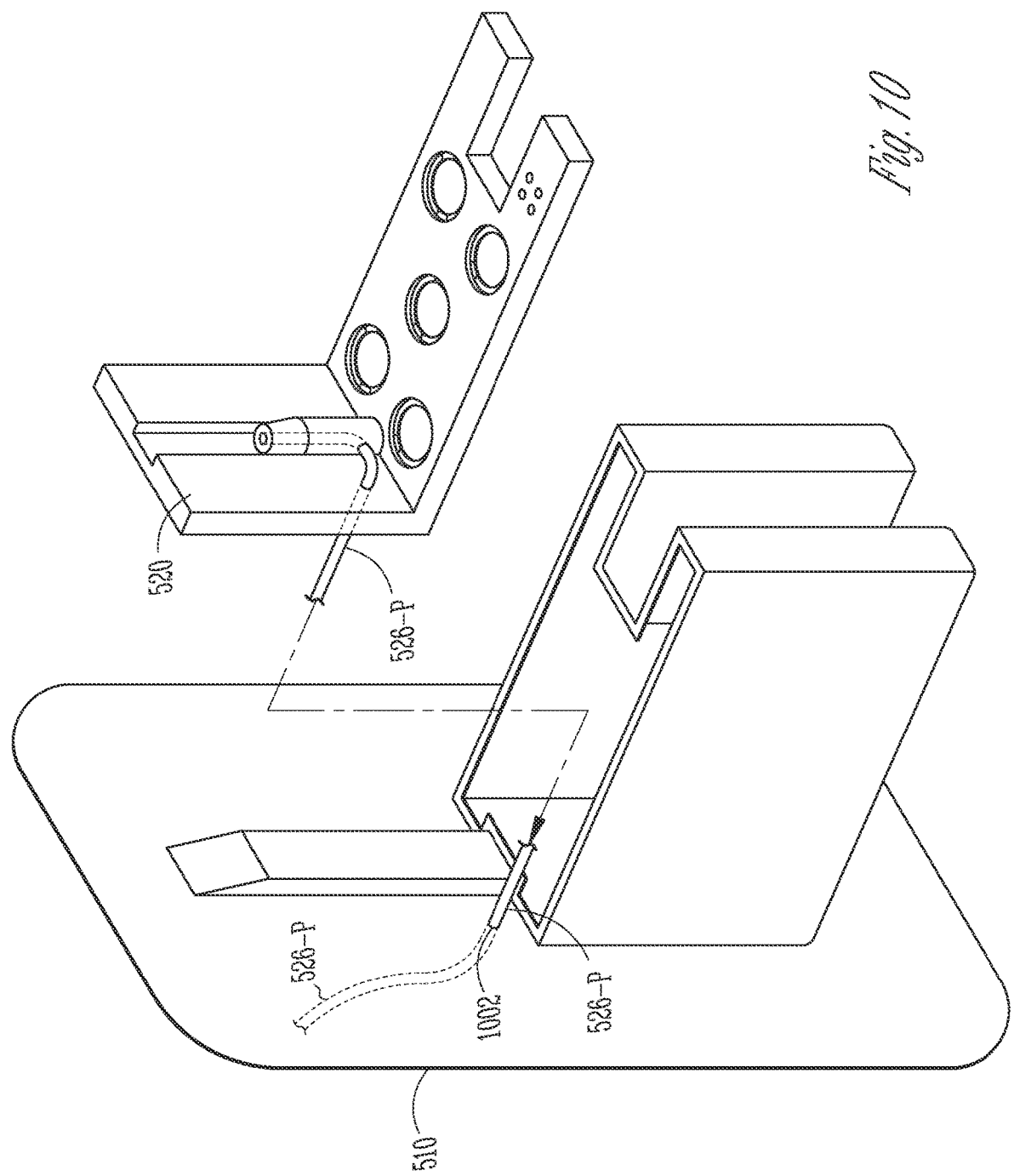
FIG. 10 is an illustrative partial top perspective view of the sterile adapter showing a proximal portion of the first optical fiber passing through an opening formed in the flange drape.

FIG. 10 is an illustrative partial top perspective view of the sterile adapter 502 showing a proximal portion 526-P of the first optical fiber 526 passing through an opening 1002 formed in the flange drape 510. The flange drape 510 is shown bent away from the upstanding guide wall 520 to better show the opening 1002 in the flange drape 510. The opening 1002 may include a slot-hole through which the proximal portion 526-P of the first optical fiber 526 may be inserted. To protect against contamination, the slot 1002 may be sealed with an adhesive strip (not shown) once the proximal portion 526-P of the first optical fiber 526 is inserted through it. A distal side of the flange drape 510 (i.e. a side of the flange drape that is adjacent the upstanding guide wall 520) is disposed in the sterile field. Thus, a proximal portion 526-P of the first optical fiber 526 on the distal side of the flange drape 510 is disposed within the sterile field. However, a proximal side of the flange drape 510 may become exposed to a non-sterile region. A proximal portion 526-P of the first optical fiber 526 disposed on the proximal side of the flange drape 510 extends inside the non-sterile cavity defined by the drape so as to reach processors located on the electronics cart 24 to process optical signals transmitted on the first and second optical fibers 526, 718. An optical coupler at an end of the second optical fiber within the non-sterile region may couple the second optical fiber for processing optical signals.

Figure 11:
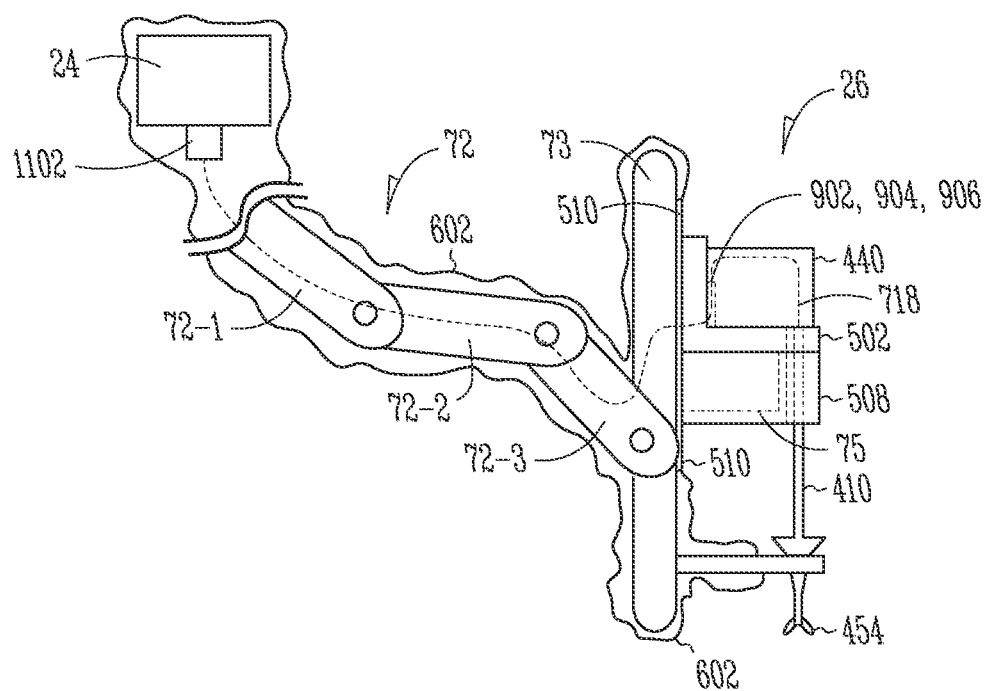
FIG. 11 is an illustrative simplified side view of showing first and second optical fibers coupled together within a surgical field and extending between a surgical instrument in a sterile field and an optical processing unit in a non-sterile field.

FIG. 11 is an illustrative simplified side view of showing first and second optical fibers 526, 718, coupled extending between a surgical instrument 26 in a sterile field and an optical processing unit 24 in a non-sterile field. The second optical fiber 718 extends along the sterile surgical instrument shaft 410. In some embodiments, the second optical fiber 526 extends inside the shaft 410. Force sensors such as fiber Bragg gratings formed in the second optical fiber 718 may produce optical signals within the second optical fiber 718 indicative of force imparted to the surgical instrument 26. The first and second optical fibers 526, 718 are optically coupled, within a sterile field at a physical junction of the sterile adapter 502 and the surgical instrument 26. The first and second optical fibers 526, 718 are coupled by an optical connector 902 comprising a first optical connector portion 904 on the sterile adapter 502 and a second optical connector portion 906 on the surgical instrument 26. The first optical fiber 526 extends from inside the sterile field, through the flange drape 510, and into a non-sterile field enclosed within the support arm drape 602, to reach an optical coupler 1102 to couple it to the processing system 24.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. As explained above, for example, engagement mechanisms other than rotatable drive members 708, rotatable drive transmission members 516, and rotatable driven members 710 may be used to transmit drive forces, and consequently in such alternative embodiments, the optical connector portions 904, 906 may not be aligned with rotatable axes of such drive, interface and driven members 708, 516, 710. Thus, the scope of the disclosure should be limited only by the following claims, and it is appropriate that the claims be construed broadly and in a manner consistent with the scope of the embodiments disclosed herein. The above description is presented to enable any person skilled in the art to create and use a surgical instrument sterile adapter with optical coupler. Various modifications to the embodiments will be readily apparent to those skilled in the art, and the generic principles defined herein may be applied to other embodiments and applications without departing from the spirit and scope of the invention. In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

What is claimed is:

1. A connector system to connect an actuator to a surgical instrument, comprising:

a drive transmission interface that includes a support structure frame that includes an inward surface region and an outward surface region and that mounts a plurality of rotatable force transmission members, having parallel axes of rotation, configured to transmit a rotational actuation force from the actuator to the surgical instrument;
a guide wall that upstands from the outward surface region of a support frame and that includes a peripheral rim portion spaced apart from the outward surface region;
a first housing that extends along the guide wall from the outward surface region part way to the peripheral rim and that defines a first internal cavity that is bounded by an internal first guide sleeve aligned parallel to the axes of rotation of a rotatable drive transmission;
a first optical fiber portion that is received within the first internal cavity, that extends along a first portion of the internal first guide sleeve, and that is aligned by the first portion of the internal first guide sleeve parallel to the axes of rotation of rotatable drive transmission members;
wherein the guide wall defines a first alignment groove that is aligned with the internal first guide sleeve parallel to the axes of rotation of the rotatable drive transmission members and that extends along a region of the guide wall between the first housing and the peripheral rim to provide a first alignment feature configured to interface with a second housing on the surgical instrument;
wherein the internal first guide sleeve includes a second portion to provide a second alignment feature, configured to interface with a second optical fiber portion on the surgical instrument that protrudes from the second housing.

2. The connector system of claim 1, wherein the first alignment groove provides a coarse alignment feature to align the first housing with the second housing on the surgical instrument and the internal first guide sleeve provides a fine alignment feature to align the first optical fiber with a second optical portion on the surgical instrument.

3. The connector system of claim 2, further comprising:
a first ferrule that receives the first optical fiber portion therein and that includes an open first end tip;
wherein an end face of the first optical fiber portion extends to the open first end tip;
wherein the first ferrule, with the first optical fiber portion received therein, extends within the first internal cavity along the first portion of the internal first guide sleeve and is aligned by the first portion of the internal first guide sleeve parallel to the axes of rotation of the rotatable drive transmission members;
wherein the first end tip provides a third alignment feature to align the end face of the first optical fiber portion with a second end face of the second optical fiber portion on the surgical instrument.

4. The connector system of claim 1, further comprising a flexible drape for establishing a sterile barrier between at least a portion of the surgical instrument and the actuator.

5. The connector system of claim 4, further comprising a flexible pouch that depends from the drive transmission interface to define a pouch cavity integrally formed with the flexible drape.

6. The connector system of claim 1, further including:
a flexible drape for establishing a sterile barrier between at least a portion of the surgical instrument and the actuator;
a flexible pouch that depends from the transmission interface to define a pouch cavity integrally formed with the flexible drape; and
wherein the guide wall upstanding from the drive transmission interface defines a passageway hole through which the first optical fiber portion extends.

7. A connector system to connect an actuator to a surgical instrument, comprising:
a drive transmission interface that includes a support structure frame that includes an inward surface region and an outward surface region and that mounts a plurality of rotatable force transmission members, having parallel axes of rotation, configured to receive a rotational actuation force from the actuator and to transmit the rotational actuation force to the surgical instrument;
a guide wall that upstands from the outward surface region of a support frame and that includes a peripheral rim spaced apart from the outward surface region;
a first housing that extends along the guide wall from the outward surface region part way to the peripheral rim and that defines a first internal cavity that is bounded by an internal first guide sleeve aligned parallel to the axes of rotation of a rotatable drive transmission;
a first optical fiber portion that is received within the first internal cavity, that extends along a first portion of the internal first guide sleeve, and that is aligned by the first portion of the internal first guide sleeve parallel to the axes of rotation of rotatable drive transmission members;
an instrument controller configured to receive the actuation force transmitted by the drive transmission interface;
a second housing on the instrument controller that includes a second optical fiber portion that protrudes from the second housing;
wherein the guide wall defines a first alignment groove that is aligned with the internal first guide sleeve parallel to the axes of rotation of the rotatable drive transmission members and that extends along a region of the guide wall between the first housing and an outer portion of the peripheral rim to provide a first alignment feature configured to interface with the second housing on the instrument controller;
wherein the internal first guide sleeve includes a second portion to provide a second alignment feature configured to interface with the second optical fiber portion on the surgical instrument that protrudes from the second housing.

8. The connector system of claim 7, wherein:
the first alignment groove provides a coarse alignment feature to align the first housing with the second housing on the surgical instrument; and
the internal first guide sleeve provides a fine alignment feature to align the first optical fiber with the second optical fiber.

9. The connector system of claim 7, further including:
a first ferrule that receives the first optical fiber portion therein and that includes an open first end tip portion;
a second ferrule that receives the second optical fiber portion therein and that includes an open second end tip portion;
wherein the second housing defines an internal second cavity that is bounded by an internal second guide sleeve;
wherein a first end face of the first optical fiber extends to the open first end tip portion of the first ferrule;

wherein a second end face of the second optical fiber extends to the open second end tip portion of the second ferrule;

wherein the first ferrule, with the first optical fiber portion received therein, extends within the first internal cavity along the first portion of the internal first guide sleeve and is aligned by the first portion of the internal first guide sleeve parallel to the axes of rotation of the rotatable drive transmission members;

wherein the second ferrule, with the second optical fiber portion received therein, partially extends within the internal second cavity along a first portion of the second guide sleeve and partially protrudes from the internal second cavity; further including:

a first spring mounted to urge the first ferrule into the internal first guide sleeve; and a second spring mounted to urge the second ferrule from the internal second guide sleeve into the internal first guide sleeve.

10. The connector system of claim 7, wherein the instrument controller includes a plurality of driven members.

11. The connector system of claim 9, wherein the open first end tip portion of the first ferrule is configured to align the open second end tip of the second ferrule inserted within the internal first guide sleeve.

* * * * *

UNITED STATES PATENT AND TRADEMARK OFFICE
CERTIFICATE OF CORRECTION

PATENT NO. : 12,023,118 B2
APPLICATION NO. : 17/475259
DATED : July 2, 2024
INVENTOR(S) : John Ryan Steger Page 1 of 1

It is certified that error appears in the above-identified patent and that said Letters Patent is hereby corrected as shown below:

On the Title Page

In item (57), in "Abstract", in Column 2, Line 3, delete "comprising." and insert --comprising:-- therefor In the Claims In Column 13, Line 20, in Claim 10, after "claim 7,", delete a linebreak In Column 13, Line 23, in Claim 11, after "claim 9,", delete a linebreak Signed and Sealed this
Seventh Day of January, 2025

Derrick Brent
*Acting Director of the United States Patent and Trademark Office*